United States Patent [19]

Rasulev et al.

[11] Patent Number: 4,994,748
[45] Date of Patent: Feb. 19, 1991

[54] SURFACE IONIZATION DETECTOR FOR ANALYZING GAS MIXTURES

[76] Inventors: Utkur K. Rasulev, prospekt Kosmonavtov, 17, kv. 3; Alexandr S. Avakov, ulitsa T.Shevchenko, 24, kv. 14; Erkinzhan G. Nazarov, Almazar, 10, kv. 115; Vladimir V. Palitsin, Junus-Abad, kvartal 5, 8, kv. 4; Irina L. Tsikanovskaya, Ts-2, 17, kv. 14, all of Tashkent, U.S.S.R.

[21] Appl. No.: 460,922
[22] PCT Filed: May 31, 1989
[86] PCT No.: PCT/SU89/00151
 § 371 Date: Feb. 1, 1990
 § 102(e) Date: Feb. 1, 1990
[87] PCT Pub. No.: WO89/12227
 PCT Pub. Date: Dec. 14, 1989

[30] Foreign Application Priority Data

Feb. 6, 1988 [SU] U.S.S.R. .............................. 4427690

[51] Int. Cl.$^5$ ............................................. G01N 27/62
[52] U.S. Cl. ...................................... 324/468; 324/464
[58] Field of Search ............... 324/459, 464, 468, 470; 73/25.01, 25.05; 313/363.1, 362.1; 436/153; 250/374, 379, 383, 384, 385.1

[56] References Cited

U.S. PATENT DOCUMENTS

| | | | |
|---|---|---|---|
| 2,576,601 | 11/1951 | Hays | 313/362.1 |
| 4,218,225 | 8/1980 | Kirchhoff | 55/140 |
| 4,282,741 | 8/1981 | Zarchy | 324/468 |
| 4,304,997 | 12/1981 | Sullivan et al. | 324/470 |
| 4,499,054 | 2/1985 | Katsura et al. | 324/468 |

FOREIGN PATENT DOCUMENTS 50-61288 5/1975 Japan .
50-128595 9/1975 Japan .

Primary Examiner—Reinhard J. Eisenzopf
Assistant Examiner—Maura K. Regan
Attorney, Agent, or Firm—Burgess, Ryan & Wayne

[57] ABSTRACT

The surface ionization detector for analyzing gas mixtures comprises a case (1) accommodating a thermoemitter placed at right angles to the direction of movement of a gas mixture and formed with electrically insulated extended ionizing elements, for example, parallel metal wires (9), each of which is connected to its current lead (11) to provide for independent regulation of heating power for each wire (9). The analyzed constituents of the gas mixture, the molecules of which are ionized through surface ionization, are ionized on the surfaces of the metal wires (9), desorbed therefrom and acted upon a potential difference of about several volts between the thermoemitter the ion collector (8) to move towards the ion collector (8) placed after the thermoemitter and made as a perforated element, for example, a metal mesh (13). The molecules of the flowing gas mixture assist in effective movement of ions from the thermoemitter to the ion collector (8) due to their location at right angles to the direction of movement of the gas mixture in the case (1).

3 Claims, 2 Drawing Sheets

SURFACE IONIZATION DETECTOR FOR ANALYZING GAS MIXTURES

TECHNICAL FIELD

The present invention relates to devices for analyzing gas mixtures, more particularly, to surface ionization detectors for analyzing gas mixtures.

BACKGROUND ART

Detectors involving surface ionization posses high sensitivity and selectivity in detecting organic compounds containing a nitrogen heteriatom. For example, the threshold in detecting tertiary amines and their derivatives reaches $10^{-14}$–$10^{-15}$ g/s. The molecules of the air and saturated hydrocarbons are not practically detected. A surface ionization detector was, thus, used to create a sensitive gas analyzer for analyzing amines and their derivatives. As a rule, a relevant analysis procedure is aimed at detecting amines in gas mixtures in the air inside work spaces presenting electric and explosion hazards as regards operating conditions and composition of analyzed mixtures.

This feature imposes limitations on gas-analyzing means designed for operation under the above conditions, more specifically, on maximum voltages required for their operations.

Furthermore, gas analyzers characterized by a high analysis rate are needed to effectively check the amine content in work spaces. The known surface ionization detectors are characterized by a limited feed rate, a disadvantage associated with the fact the temperature of a thermoemitter is to a large measure dependent on the flow of the analyzed mixture.

There is known a diode device for analyzing organic compounds directly in the air (cf. E. Ya. Zandberg, N. I. Ionov, V. I. Paleev, U. K. Rasulev: "Indicator aminov v atmosphere na osnove galoidnogo techneiskatelya", Zhurnal Tekhnichoskoy Physiki, 1984, Volume 54, pp 1855, 1856). This device essentially represents a haloid leak detector and contains in a case a cylindrical thermoemitter made of molybdenum and heated on the inside with a platinum heater, and also an ion collector encompassing with a gap the cylindrical thermoemitter.

The mixture to be analyzed is directed into the gap between the cylindrical thermoemitter and the ion collector and a part of ionized molecules getting on the surface of the thermoemitter forms positive ions which are acted upon by an electric field and, in effect, reach the ion collector wherein they are recorded.

However, the foregoing device has been generally unsatisfactory due to the need for using voltages as great as 200 V for collecting ions formed on the surface of the thermoemitter. Such operating voltages prevent utilization of the disclosed device in premises characterized by electric and explosion hazards.

The closest prior art device is a surface ionization detector for analyzing amine gas mixtures (cf. E. Ya. Zandberg, A. G. Kamenev, V. I. Paleev, U. K. Rasulev: "Visokochuvstvitelny detector aminov i ikh proizvodnikh", Zhurnal Analyticheskoy khimii, 1980, Volume 35, No. 6, pp 1188-1194), which comprises a case with a cylindrical collector, housing a directly heated thermoemitter of coiled molybdenum wire whose axis is disposed in the direction of movement of the analyzed mixture in the case of the surface ionization detector. Molecules of the analyzed mixture getting into the thermoemitter are ionized and gathered at the ion collector under the action of potential applied to the thermoemitter, which is positive relative to the ion collector. The ions are detected int eh direction perpendicular to the direction of movement of the analyzed mixture in the case of the surface ionization detector. Therefore, potential as great as 200 to 300 V should be applied between the thermoemitter and the ion collector to provide for a condition when, after desorption from the thermoemitter, the ions are effectively gathered at the collector.

Moreover, the use of the thermoemitter representing a spiral leads to eddy flows of the analyzed mixture, which also necessitates the application of high potential.

However, the utilization of voltages as great as 200 to 300 V for effective collection of ions formed on the surface of the thermoemitter prevents the use of the disclosed device in premises characterized by electric and explosion hazards.

DISCLOSURE OF THE INVENTION

The invention resides in providing a surface ionization detector for analyzing gas mixtures, in which a novel construction of a thermoemitter and an ion collector and their proper location with respect to a gas mixture flow would make it possible to increase operational safety and reliability thereof.

The object of the invention is to create a surface ionization detector for analyzing gas mixtures, which is characterized by increase operational reliability and safety and a higher analysis rate with high ionizing effectiveness.

There is provided a surface ionization detector for analyzing gas mixtures, comprising a case with inlet and outlet connections for a mixture to be analyzed, housing a thermoemitter with current leads and an ion collector connected to an electrometric lead, said thermoemitter and said ion collector being mounted with a gas, in which, according to the invention, the ion collector is made as a perforated element located after the thermoemitter in the direction of movement of the analyzed gas mixture substantially at right angles to the direction of its movement in the case, whereas the thermoemitter is formed with at least one row of extended ionizing elements electrically insulated from one another, each ionizing element being connected to its own current lead.

It is advantageous that the flat perforated element of the ion collector should represent a metal mesh.

It is also of advantage that the extended ionizing elements of the thermoemitter should be formed with parallel metal wires electrically insulated from one another.

A novel construction of the thermoemitter and the ion collector, their relative location and the movement of the analyzed gas mixture in the direction perpendicular tot eh thermoemitter and the ion collector permit distribution therebetween the entire flow of the analyzed gas mixture. With the total analysis rate being essentially unchanged, the gas mixture is made to pass each element of the thermoemitter at a slower speed whereby maximum power applied to separate elements of the thermoemitter during the analysis procedure can be substantially decreased.

BRIEF DESCRIPTION OF THE DRAWINGS

The invention will now be described further with reference to specific embodiments thereof, taken in conjunction with the accompanying drawings wherein.

BEST MODE OF CARRYING OUT THE INVENTION

Figure 1:
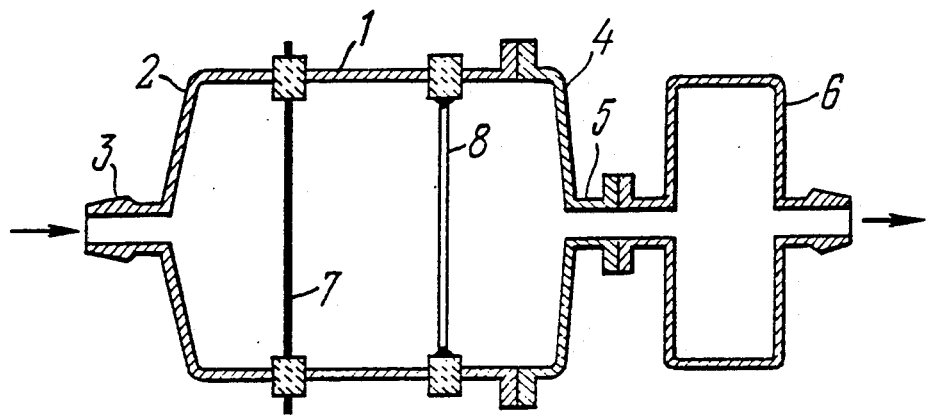
FIG. 1 shows diagrammatically a surface ionization detector for analyzing gas mixtures according to the invention.

The proposed surface ionization detector for analyzing gas mixtures comprises a case 1 with its one end wall 2 mounting an inlet connection 3. Another end wall 4 of the case 1 is a removable structure accommodating an outlet connection 5 arranged in line with the inlet connection 3. A gas-mixture flow agitator 6 is connected to the outlet connection 5. The case 1 can be made of a suitable metal or dielectric. Located in the case 1 in close proximity to the inlet connection 3 is a thermoemitter 7 installed at right angles to the direction of movement of the analyzed gas mixture n the case 1. Said thermoemitter comprises at last one row of substantially parallel extended ionizing elements electrically insulated from one another. Each extended ionizing element is connected to its own current lead. An ion collector 8 is placed after the thermoemitter 7 in the case 1 at right angles to the direction of movement of the flowing gas mixture. The value of the gap between the thermoemitter 7 and the ion collector 8 has only slight effect on measured current and is primarily determined by a specific construction of the case 1 of the surface ionization detector. The ion collector 8 is made as a perforated element connected to an electrometric lead.

A preferred embodiment of the proposed surface ionization detector for analyzing gas mixtures will be described below.

Figure 2:
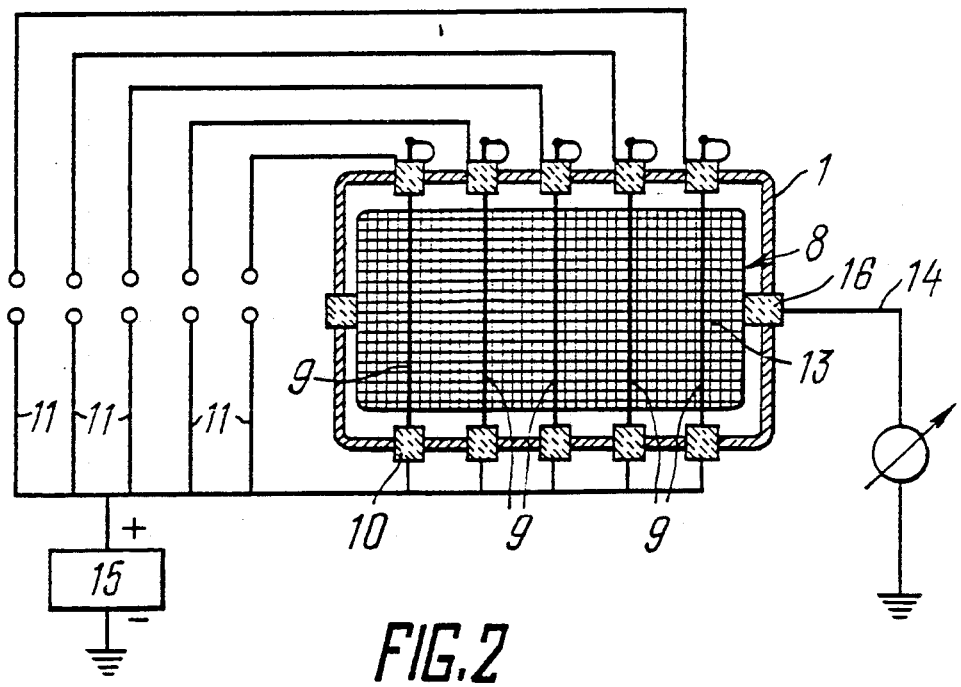
FIG. 2 depicts a preferred embodiment of an ion collector and a thermoemitter according to the invention, and FIG. 3 give the volt-ampere characteristics of the surface ionization detector for analyzing gas mixtures according to the invention.

In the illustrated embodiment the case 1 (FIG. 2) is a metal structure. The thermoemitter 7 is formed with a set of metal wires 9 arranged parallel to one another in one plane in the case 1. The distance between the metal wires 9 of the thermoemitter 7 is chosen to be approximately equal to the diameter of one wire 9. Therefore, the number of the metal wires 9 of the thermoemitter 7 is set depending on the linear dimensions of the case 1 of the surface ionization detector, which are in turn selected to ensure a desired rate in analyzing gas mixtures. Each metal wire 9 is insulated form the case 1 with a ceramic washer 10 and connected to its own current lead 11, a feature allowing independent heating of each metal wire 9. Each metal wire 9 is tensioned by a spring-loaded fastener securing one of the end of the metal wire 9 to the current lead 11.

The ion collector 8 is formed with a metal mesh 13. The ion collector 8 is connected to an electrometric lead 14. A potential difference between the thermoemitter 7 and the ion collector 8 is created by applying to each metal wire 9 of the thermoemitter 7 positive potential from a voltage source 15 through the current leads 11.

The surface ionization detector forming the subject of the present invention operates as follows. At a preliminary stage, the surface ionization detector is adjusted by selecting a heater voltage for each metal wire 9 (FIG. 2) of the thermoemitter 7. This is done by disconnecting the outlet connection 5 (FIG. 1) from the case 1 and connecting the gas mixture flow agitator 6 to the inlet connection 3 of the case 1 to produce ordered motion of the gas being the basic constituent of the analyzed mixture in the direction from the thermoemitter 7 to the collector 8. The as flow is set to correspond to the operating rate of flow of the analyzed gas mixture. Connected to the end wall 4 is an instrument for measuring the temperature of each metal wire 9, for example, a micropyrometer (not shown in FIG. 2) used to check the brightness temperature of the metal wires 9. The heater voltage is chosen to provide for the most uniform temperature distribution over the entire surface of the thermoemitter 7. Power distribution within the metal wires 9 will be characteristic of a particular structure of the surface ionization detector and the flow rate of a given gas mixture to be analyzed. The chosen heater voltages of the metal wires 9 of the thermoemitter 7 should be maintained at a constant level while the surface ionization detector is in operation.

On completion of the adjustment procedure, the gas-mixture flow agitator 6 is disconnected form the inlet connection 3 and connected to the end wall 4 of the case 1 through the outlet connection 5. The gas-mixture flow agitator 6 brings about ordered motion of the analyzed gas mixture flowing through the case 1 of the surface ionization detector. The metal wires 9 of the thermoemitter 7 are fed with the chosen heater voltages. To create a potential difference between the thermoemitter 7 and the ion collector 8, potential is applied form the voltage source 15 to the thermoemitter 7 through the current leads 11.

The analyzed constituents of the gas mixture are ionized on the surfaces of the heated metal wires 9 and then thermally desorbed therefrom. (The molecules of said analyzed constituents are ionized through surface ionization).

The desorbed ions move towards the ion collector 8 due to the action of the flowing gas mixture and a potential difference between the ion collector 8 and the thermoemitter 7. In this case the molecules of the flowing gas mixture do not prevent but on the contrary facilitate the movement of the ions from the thermoemitter 7 to the ion collector 8 due to perpendicular location thereof relative to the direction of movement of the analyzed gas mixture in the case 1. Conditions are, thus, created for effectively gathering the ions at the collector 8 even of a potential difference is about several volts. The use of the ion collector representing the metal mesh 13 and its location after the thermoemitter 7 int eh direction of movement of the gas mixture do not impair ordered motion of the flowing gas mixture under test nd provide for effective gathering of ions at the collector 8.

The utilization of the thermoemitter 7 formed with a set of parallel extended metal wires 9 permits distributing among the metal wires 9 the entire flow of the analyzed gas mixture. Without essentially changing the total analysis rate, the speed at which the analyzed mixture passes each metal wire 9 of the thermoemitter 7 is appreciably decreased. A lower flow rate decreases heat removal from each metal wire 9. Therefore, lower excess heating power s required to maintain the operating temperature of each metal wire 9 and the thermoemitter as a whole during a dynamic analysis. Furthermore, conditions may be created in which the temperature of the thermoemitter 7 does not change in the event of any unforeseen interruption of the gas mixture flow. Uniform temperature distribution over the length of each wire 9 is attained due to the fact that all the wire elements are made sufficiently extended. Independent current leads 11 to each metal wire 9 allow separate regulation of heating power so that the temperatures of these wires are equaled.

The ionized molecules of the analyzed gas mixture are thermally desorbed from the surfaces of the metal wires 9 and move in a potential field from the thermoemitter 7 to the collector 8.

The ion current is supplied through the electrometric lead 14 to a charge amplifier and suitably recorded. The analysis of the mixture is made with respect to the magnitude of the recorded signal. The generated signal is indicative of the fact that the analyzed mixture contains substances (amines, hydrazines and their derivatives) ionized through surface ionization. The magnitude of the signal will characterize the quantity of organic compounds.

The thermoemitter and the ion collector according to the invention can be designed in another suitable manner. For example, ionized molecules can effectively reach the ionizing elements of the thermoemitter 7 if the latter are arranged in two or more rows so that the ionizing elements of the subsequent row are placed between tow elements of the preceding row relative to the direction of movement of the mixture analyzed in the detector. Furthermore, the extended elements of he thermoemitter 7 can be formed with thin bands. The ion collector 8 can comprises not only a metal mesh but also any other conducting element having a perforated surface and providing for free passage of the analyzed mixture therethrough with effective collection of ions from the flow. Such an element may, for example, represent microchannel plates. Since the ion collector 8 is located after the thermoemitter 7 relative to the direction of gas flow in the surface ionization detector, the thermoemitter 7 is less likely to contaminated with impurities from the material of the ion collector 8, which makes less stringent the requirements for purity and quality of the material of the ion collector 8.

An example of the proposed surface ionization detector is described below.

Figure 3:
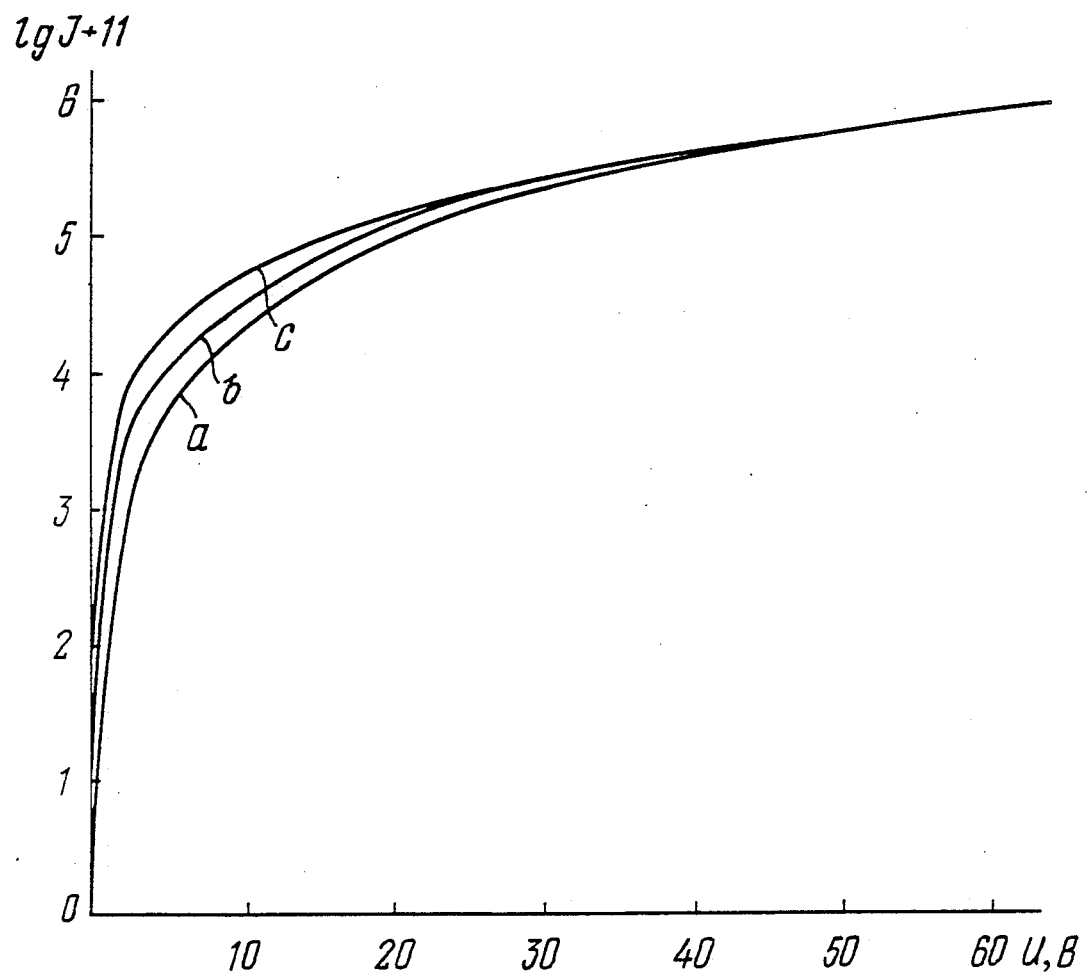

The manufactured surface ionization detector included a thermoemitter composed of five independently heated ionizing elements. The thermoemitter 7 was made of molybdenum wire with the diameter $d=1.2$ mm. The length of the working portion of each ionizing element of the thermoemitter 7 was 25 mm. the elements of the thermoemitter 7 were disposed in one plane with a gap of 1 mm therebetween and secured to the case 1 of the surface ionization detector through insulating elements. The total area of the surface ionization detector occupied by the ionizing elements was 300 $mm^2$. Under operating conditions the temperature of the ionizing elements of the thermoemitter 7 was maintained at 650° K. The power of about 5 to 6 W was supplied to each thermoemitter 7 in the dynamic mode. The ion collector 8 was made of the metal mesh 13 stretched on a frame which was rigidly secured to the case 1 by means of insulating washers 16. These washers were simultaneously used to insulate the electrometric lead 14 from the case 1. The collector 8 was 5 mm away form the thermoemitter 7. The characteristics of the surface ionization detector were checked using calibrated triethylamine-air mixtures prepared in a gas dynamic installation. So, a triethylamine-air mixture having a flow rate of 66 ml/min and the concentration C equaling $2.5 \cdot 10^{-5}$ g/l was doped with clean air having a regulated flow rate. The surface ionization detector was receiving the same amount of ionized substances per unit time at a varying speed of the mixture passed therethrough. FIG. 3 shows curves indicated of the voltampere characteristics of the surface ionization detector according to the invention. In the drawing the curve (a) illustrates the case where the surface ionization detector was fed with a triethylamine-air mixture having a flow rate of 66 ml/min (without addition of clean air); the curve (b) was obtained with a flow rate of 465 ml/min; and the curve (c) was obtained with a flow of 1500 ml/min. The curves (b) and (c) illustrate the case where clean air was added to the initial mixture. It is apparent that in the proposed surface ionization detector the formed ions can be effectively collected with the potential difference between the thermoemitter and the collector being as small as 10 to 15 V. By comparison, in the prior art detectors a voltage as great as 200 to 300 V should be applied between the emitter and the collector to provide for effective collection of ions.

Furthermore, in the prior art detectors the maximum analysis rate is limited to about 300 ml/min since at a higher rate the ionizing effectiveness of the detector is reduced due to strong cooling of its end face.

Referring to the curves of FIG. 3 it is apparent that in the proposed surface ionization detector the ionizing effectiveness does not essentially change with the analysis rate increased to 1500 ml/min. (In the illustrated plots the limiting current values coincide). In as much as the temperature of the elements of the thermoemitter 7 is only slightly affected by the gas flow, operation of the surface ionization detector is not impaired when the flow of the analyzed gas mixture is interrupted with the ionizing elements of the thermoemitter 7 being activated, an advantage substantially increasing operational reliability of the proposed surface ionization detector.

Thus, the surface ionization detector according to the present invention has the following advantages over the prior art.

Its operational reliability is appreciably higher than that of the known surface ionization detectors.

In the proposed surface ionization detector the analysis rate can be made higher by increasing its aperture and, accordingly, the number of ionizing elements.

Moreover, operational safety of the proposed surface ionization detector is substantially increased owing to the fact that the accelerating voltage is reduced at least ten-fold. Its high ionizing effectiveness is another positive feature.

Industrial Applicability

The invention can find applications in various gas dynamic devices utilizing the surface ionization effect and designed for operation in conditions characterized by electric and explosion hazards.

We claim:

1. A surface ionization detector for analyzing gas mixtures, comprising a case (1) with an inlet connection (3) and an outlet connection (5) to bring in and out a gas mixture to be analyzed, housing a thermoemitter (7) with current leads (11) and an ion collector (8) connected to an electrometric lead (14), said thermoemitter and said ion collector being separated by a gap, characterized in that the ion collector (8) is made as a perforated element placed after the thermoemitter (7) in the direction of movement of the analyzed gas mixture substantially at right angles to the direction of its movement in the case (1), whereas the thermoemitter (7) is formed with at least one row of extended ionizing elements electrically insulated from one another, each element being connected to its own current lead (11).

2. A surface ionization detector for analyzing gas mixtures as claimed in claim 1, characterized in that the perforated element of the ion collector (8) represents a metal mesh (13).

3. A surface ionization detector as claimed in claim 1, characterized in that the extended ionizing elements of the thermoemitter (7) are made as parallel metal wires (9).

* * * * *